United States Patent
Miller et al.

(10) Patent No.: US 9,701,652 B2
(45) Date of Patent: Jul. 11, 2017

(54) FORMATION OF 2,5-FURAN DICARBOXYLIC ACID FROM ALDARIC ACIDS

(71) Applicant: BOARD OF TRUSTEES OF MICHIGAN STATE UNIVERSITY, East Lansing, MI (US)

(72) Inventors: Dennis J. Miller, Okemos, MI (US); Lars Peereboom, Haslett, MI (US); Evan Wegener, Haslett, MI (US); Matthew Gattinger, Lake Orion, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 15/359,735

(22) Filed: Nov. 23, 2016

(65) Prior Publication Data
US 2017/0144982 A1    May 25, 2017

Related U.S. Application Data

(60) Provisional application No. 62/259,815, filed on Nov. 25, 2015.

(51) Int. Cl.
*C07D 307/02* (2006.01)
*C07D 307/68* (2006.01)

(52) U.S. Cl.
CPC ................. *C07D 307/68* (2013.01)

(58) Field of Classification Search
CPC .................................................... C07D 307/68
USPC ......................................................... 549/485
See application file for complete search history.

(56) References Cited

U.S. PATENT DOCUMENTS

| | | | |
|---|---|---|---|
| 3,326,944 | A | 6/1967 | Lew |
| 7,411,078 | B2 | 8/2008 | Miura et al. |
| 8,242,292 | B2 | 8/2012 | Yutaka et al. |
| 2014/0295508 | A1 | 10/2014 | Yoshikuni et al. |
| 2015/0065749 | A1* | 3/2015 | Van Es ............... B01J 23/52 562/531 |
| 2015/0086721 | A1 | 3/2015 | Texter |

FOREIGN PATENT DOCUMENTS

FR          2723945        *  3/1996

OTHER PUBLICATIONS

Albonetti et al., Conversion of 5-hydroxymethylfurfural to 2,5-furandicarboxylic acid over Au-based catalysts: Optimization of active phase and metal-support interaction, Applied Catalysis B: Environmental, 163:520-30 (2015).
Burgess et al., Chain mobility, thermal, and mechanical properties of poly(ethylene furanoate) compared to poly(ethylene terephthalate, Macromolecules, 37:1383-91 (2014).
Burgess et al., Oxygen sorption and transport in amorphous poly-(ethylene furanoate), Polymer, 55:4748-56 (2014).
Dutta et al., A brief summary of the synthesis of polyester building-block chemicals and biofuels from 5-hydroxymethylfurfural, Chem. Phys. Chem., 77:1-15 (2012).
Gao et al., Efficient oxidation of biomass derived 5-hydroxymethlfurfural into 2,5-furandicarboxylic acid catalyzed by Merrifield resin supported cobalt porphyrin, Chem. Eng. J., 270:444-9 (2015).
Jadhav et al., Green chemical conversion of fructose into 5-hydroxymethylfurfural (HMF) using unsymmetrical dicationic ionic liquids under mild reaction conditions, Chem. Eng. J., 243:92-8 (2014).
Jain et al., Selective oxidation of 5-hydoxymethyl-2-furfural to furan-2,5-dicarboxylic acid over spinel mixed metal oxide catalyst, Catalysis Commun., 58:179-82 (2015).
Koopman et al., Efficient whole-cell biotransformation of 5-hydroxymethylfurfural into FDCA, 2,5-furandicarboxylic acid, 101:6291-6 (2010).
Kurian et al., Feedstocks, logistics and pre-treatment processes for sustainable lignocellulosic biorefineries: A comprehensive review, Renewable and Sustainable Energy Rev., 25:205-19 (2013).
Lolli et al., Insights into the reaction mechanism for 5-hydroxymethylfurfural oxidation to FDCA on bimetallic Pd—Au nanoparticles, Applied Catalysis A: General, 504:408-19 (2015).
Molina et al., "Production of 2,5-Furandicarboxylic Acid from Biomass-Derived Aldaric Acids," Presented at the 2016 AICHE Annual Meeting in San Francisco, CA (Nov. 13-18, 2016).
Pedersen et al., Synthesis of 5-hydroxymethylfurfural (HMF) by acid-catalyzed dehydration of glucose-fructose mixtures, Chem. Eng. J., 273:455-64 (2015).
Taguchi et al., One-step Synthesis of Dibutyl Furandicarboxylates from Galactaric Acid, Chem. Lett., 237:50-1 (2008).
Tong et al., Biomass into chemicals: conversion of sugars to furan derivatives by catalytic processes, Applied Catalysis A: General, 385:1-13 (2010).
Vilela et al., The quest for sustainable polyesters—insights into the future, Polym. Chem., 5:3119 (2014).
Yu et al., Chemosynthesis and characterization of fully biomass-based copolymers of ethylene glycol, 2,5-furandicarboxylic acid, and succinic acid, J. Appl. Polym. Sci., 130:1415-20 (2013).
Zhang et al., Advances in catalytic production of bio-based poly-ester monomer 2,5-furandicarboxylic acid derived from lignocel-lulosic biomass, Carbohydrate Polymers, 130:420-8 (2015).

* cited by examiner

*Primary Examiner* — T. Victor Oh
*Assistant Examiner* — Taylor V Oh
(74) *Attorney, Agent, or Firm* — Marshall, Gerstein & Borun LLP

(57) ABSTRACT

The disclosure relates to a method for forming 2,5-furan dicarboxylic acid (FDCA) from aldaric acids. The aldaric acids are dehydrating and cyclizing via acid catalysis to form the FDCA product. Aldaric acids such as galactaric acid, gularic acid, mannaric acid, and glucaric acid can be used in the disclosed method, and the aldaric acids can be obtained from form renewable biomass sources which contain pectin, alginate, and/or other biomass carbohydrates. The FDCA can be used as a renewable feedstock for consumer product polymeric materials such as polyalkylene furoate polymers.

21 Claims, No Drawings

FORMATION OF 2,5-FURAN DICARBOXYLIC ACID FROM ALDARIC ACIDS

CROSS REFERENCE TO RELATED APPLICATION

Priority is claimed to U.S. Provisional Application No. 62/259,815 filed Nov. 25, 2015, which is incorporated herein by reference in its entirety.

STATEMENT OF GOVERNMENT INTEREST

None.

BACKGROUND OF THE DISCLOSURE

Field of the Disclosure

The disclosure relates to a method for forming 2,5-furan dicarboxylic acid (FDCA) from aldaric acids. The aldaric acids are dehydrating and cyclizing via acid catalysis to form the FDCA product. The aldaric acids can be obtained from renewable biomass sources which contain pectin, alginate, and/or other biomass carbohydrates. The FDCA can be used as a feedstock for polyalkylene furoate polymers.

Background

Most current effort toward producing FDCA is centered around a chemical pathway involving the dehydration of glucose or (more easily) fructose to form hydroxymethyl furfural (HMF), which is then oxidized to FDCA by a variety of catalysts. There are two challenges with this route at present: one is that the intermediate HMF is a difficult molecule to isolate, because it has low volatility and low decomposition temperature. The second is that the oxidation of HMF to FDCA is not particularly efficient and requires precious metal catalysts, dilute reaction conditions, and control of pH. Because of these challenges, no commercial production of FDCA from HMF exists at present.

Another approach is the formation of FDCA esters from galactaric acid. Specifically, dibutyl FDCA ester from butyl galactarate was formed via the action of sulfuric acid in butanol solvent; this reaction proceeded readily but was accompanied by the formation of dibutyl sulfate which eventually consumed the sulfuric acid and quenched the reaction.

SUMMARY

In one aspect, the disclosure relates to a method for forming 2,5-furan dicarboxylic acid (FDCA), the method comprising: providing a reaction medium comprising a 6-carbon aldaric acid and an acid catalyst (e.g., a liquid reaction medium with the aldaric acid and acid catalyst therein); and dehydrating and cyclizing the aldaric acid in the reaction medium (e.g., under temperature and pressure conditions suitable to drive the acid catalysis of the dehydration and cyclization reactions) to form 2,5-furan dicarboxylic acid (FDCA) as a reaction product. An aldaric acid is a dicarboxylic acid derivative of a sugar. The 6-carbon aldaric acids useful for formation of FCDA generally have the formula HOOC—(CHOH)$_4$—COOH. Aldaric acids with any combination of chiral carbon atoms (—(CHOH)—) may be used, as isomeric differences arising therefrom in the original aldaric acid are eliminated upon dehydration and cyclization to form FDCA product. Examples of aldaric acids suitable in the disclosure method include those available from renewable biomass sources, for example including galactaric acid, gularic acid, mannaric acid, and glucaric acid, which are variously obtainable from pectin, alginate, and/or other biomass carbohydrates (e.g., starch, glucose) in various biomass sources.

Various refinements and embodiments of the disclosed methods are possible.

In a refinement, the aldaric acid comprises galactaric acid (or mucic acid; a galactose di-acid analog obtainable by oxidation of galacturonic acid or of galactose with an acid). For example, the method can further comprise oxidizing galacturonic acid to form galactaric acid; and adding the galactaric acid to the reaction medium. Alternatively, the method can further comprise extracting pectin from a biomass material (e.g., pulp, extract, or other residue); hydrolyzing the pectin to form galacturonic acid; oxidizing the galacturonic acid to form galactaric acid; and adding the galactaric acid to the reaction medium. The biomass material can be selected from the group consisting of sugarbeet pulp, apple pomace, citrus pulp, and combinations thereof.

In another refinement, the aldaric acid comprises at least one of gularic acid and mannaric acid (di-acid analogs obtainable by oxidation of guluronic acid and mannuronic acid, respectively). For example, the method can further comprise oxidizing at least one of guluronic acid and mannuronic acid to form at least one of gularic acid and mannaric acid, respectively; and adding the at least one of gularic acid and mannaric acid to the reaction medium. Alternatively, the method can further comprise extracting alginate from a biomass material (e.g., pulp, extract, or other residue); hydrolyzing the alginate to form at least one of guluronic acid and mannuronic acid (e.g., in acid form or salt form, such as sodium or potassium guluronate or mannuronate); oxidizing the at least one of guluronic acid and mannuronic acid to form at least one of gularic acid and mannaric acid, respectively; and adding the at least one of gularic acid and mannaric acid to the reaction medium. The biomass material can comprise macro algae (e.g., brown algae, (brown) seaweed).

In another refinement, the aldaric acid comprises glucaric acid (or saccharic acid; a glucose di-acid analog obtainable by oxidation of glucose such as with an acid). Direct oxidation of glucose to glucaric acid can be part of a larger process in which biomass is first processed to extract or otherwise obtain biomass carbohydrates such as starch and/or cellulose from the biomass, which biomass carbohydrates can be then hydrolyzed or otherwise converted by known techniques (e.g., enzymatic hydrolysis, acid hydrolysis) to the glucose used for glucaric acid and (ultimately) FDCA formation.

In another refinement, the reaction medium further comprises an ionic liquid. The ionic liquid comprises a cationic moiety selected from the group consisting of a pyridinium, pyridazinium, pyrimidinium, pyrazinium, oxazinium, thiazinium, imidazolium, pyrazolium, thiazolium, isothiazolium, oxazolium, isoxazolium, and triazolium cationic moieties. The ionic liquid can further comprise one or more organic substituents selected from the group consisting of alkyl groups and aryl groups (e.g., linear or branched alkyl groups of 1 to 4 or 1 to 20 carbon atoms (e.g., substituted or unsubstituted), aryl groups of 6 to 20 carbon atoms (e.g., substituted or unsubstituted)). The ionic liquid can further comprise a counter anion selected from the group consisting of sulfate, hydrogen sulfate, nitrate, fluoride, chloride, bromide, iodide, methyl sulfonate, and fluoroborate anion. The acid catalyst can comprise an acid corresponding to the counter anion of the ionic liquid (e.g., sulfuric acid (i.e., corresponding to sulfate or hydrogen sulfate), nitric acid, hydrofluoric acid, hydrochloric acid, hydrobromic acid, hydroiodic acid, methyl sulfonic acid, and fluoroboric acid).

Various acid catalysts may be used. In a refinement, the acid catalyst is selected from the group consisting of sulfuric acid, nitric acid, hydrofluoric acid, hydrochloric acid, hydrobromic acid, hydroiodic acid, methyl sulfonic acid, and fluoroboric acid. In another refinement, the acid catalyst is selected from the group consisting of a liquid phase organic sulfonic acid (e.g., a sulfonic acid including a linear or branched alkyl group of 1 to 4 or 1 to 20 carbon atoms (e.g., substituted or unsubstituted), or aryl group of 6 to 20 carbon atoms (e.g., substituted or unsubstituted) attached to a sulfonic acid group).

Various refinements and embodiments of the disclosed methods are possible. For example, the reaction medium can be substantially free from water (e.g., during and/or before dehydration and cyclization, although water can be added thereafter to precipitate and recover the FDCA product; for example, less than 1 wt. %, 0.1 wt. %, or 0.01 wt. % water in the reaction medium). In another refinement, the reaction medium is substantially free from alcohols (e.g., during and/or before dehydration and cyclization, thereby preventing formation of FDCA ester derivatives; for example, less than 1 wt. %, 0.1 wt. %, or 0.01 wt. % alcohols in the reaction medium, where the alcohols can include alkyl alcohols such as methanol, ethanol, propanol, butanol, etc.). In another refinement, the method further comprises separating the FDCA reaction product from the reaction medium (e.g., by precipitation from the reaction medium, such as by addition of water thereto, and then optionally filtering or otherwise separating the FDCA precipitate, where it can be dried and/or further purified as desired). In another refinement, the method comprises reacting and dehydrating the aldaric acid in the reaction medium at a temperature ranging from 50° C. to 200° C. (e.g., at least 50° C., 70° C., 90° C., or 100° C. and/or up to 100° C., 120° C., 150° C., or 200° C.). In another refinement, the method comprises reacting and dehydrating the aldaric acid in the reaction medium at a pressure equal to or less than atmospheric pressure (e.g., at least 0.001 bar, 0.01 bar, 0.1 bar, 0.2 bar, or 0.5 bar and/or up to 0.2 bar, 0.5 bar, 0.8 bar, 0.9 bar, 1.0 bar, or 1.01325 bar).

While the disclosed compounds, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

The disclosure relates to a method for forming 2,5-furan dicarboxylic acid (FDCA) from aldaric acids. The aldaric acids are dehydrating and cyclizing via acid catalysis to form the FDCA product. Aldaric acids such as galactaric acid, gularic acid, mannaric acid, and glucaric acid can be used in the disclosed method, and the aldaric acids can be obtained from form renewable biomass sources which contain pectin, alginate, and/or other biomass carbohydrates (e.g., starch, glucose). The FDCA can be used as a renewable feedstock for consumer product polymeric materials such as polyalkylene furoate polymers, for example polyethylene furoate polymers such as a poly(ethylene furandicarboxylate) ester obtained by the acid-catalyzed condensation polymerization of FDCA and ethylene glycol.

In an aspect, the disclosure relates to the conversion of galactaric acid derived from pectin in waste agricultural products to 2,5-furandicarboxylic acid (FDCA). The disclosed methods convert the pectins found in agricultural byproducts such as sugar beet pulp, apple pulp, and citrus peel to FDCA, a building block for a new generation of polymeric materials, via an intermediate aldaric acid obtainable form the agricultural byproducts. FDCA can be polymerized with ethylene glycol to form poly(ethylene-difuroate) (PEF), a chemical analog to the ubiquitous poly(ethylene terephthalate) (PETE) used for plastic bottles and packaging. PEF has physical properties similar to PETE but has vapor barrier properties that are significantly superior to PETE, thus opening new opportunities for its use in packaging applications where glass or metal was previously required. The disclosed methods can produce FDCA from pectin via several steps including extraction of pectin from agricultural byproducts, hydrolysis of pectin to its monomer galacturonic acid, oxidation of the monomer to galactaric acid, and cyclization and dehydration of galactaric acid to FDCA. In other embodiments, the methods can be applied to use alginate polymers that constitute approximately 30% of macroalgae (seaweed) as a feedstock to form aldaric acids.

The formation of FDCA from biomass carbohydrates is attractive as a component of polyethylene furanoate ester (PEF), a polymer analog to the ubiquitous, petroleum-based polyethylene terephthalate ester (PETE) that constitutes most plastic drink bottles. PEF has superior vapor barrier properties over PETE (e.g., 4× to 10× better resistance to oxygen transport, 2× to 4× better resistance to carbon dioxide and water transport) and can be used advantageously for plastic drink bottles, for example in applications where metal or glass is currently used.

The disclosed method provides a different route to FDCA, not via HMF as described above, but via formation and conversion of C6 dicarboxylic acids, more generally known as aldaric acids, that are readily obtained from pectin and macroalgae via oxidation of the carbohydrate monomers that they are composed of. These biomass sources are well known and have long histories as food additives, but they have historically been considered as less viable feed stocks than cellulosic or starch for biofuels or chemicals production. Nevertheless, they are available in large quantities in agricultural wastes such as sugar beet pulp, apple pomace, and citrus peels, and their alternative carbohydrate structures make them suitable starting materials for production of FDCA via aldaric acids.

Current global PETE production is approximately $28 \times 10^6$ metric tons (60 billion lb), and alternative PEF-based packaging materials could replace a significant fraction of PETE production. Table 1 below shows global production of several agricultural byproducts and the potential FDCA yield from a 100% efficient process. There are sufficient agricultural byproducts to supply PEF-based packaging materials on the same scale as current PETE production.

Suitable feed stocks for the proposed process can include residual products from processing of various food crops, for example sugar beet pulp and apple pomace. At present, these residues are sold almost exclusively as animal feed, bringing limited revenue and, without a secure market, the potential liability of requiring landfilling to dispose of unsold materials. The proposed process thus provides a value-added, commodity product use for agricultural byproducts that would otherwise be waste material or have very limited value.

TABLE 1

Agriculture residues from Michigan and other locations

| Residue | Annual Production (metric ton) | | Composition (wt %) | | | Potential Global FDCA Yield (metric ton) |
|---|---|---|---|---|---|---|
| | Michigan | World-wide | Pectin | Hemi-cellulose | Cellulose + Other | |
| Sugarbeet pulp | $1.7 \times 10^5$ | $13 \times 10^6$ | 20 | 52 | 28 | $3 \times 10^6$ |
| Apple pomace | $2 \times 10^5$ | $2.3 \times 10^6$ | 22 | 40 | 38 | $3.6 \times 10^6$ |
| Citrus pulp | $15 \times 10^6$ (US) | $50 \times 10^6$ | 20 | 50 | 30 | $12 \times 10^6$ |

Pectin is a polymer of 1,4-α-D-galacturonic acid that is partially methylated at the C6 carboxyl group and partially acetylated at the C2 and C3 hydroxyls. The polymer exists in three forms: a linear structure (homogalacturonan, HG) and two branched chained structures (rhamnogalacturonans, RG-1 and RG-2). The exact pectin structure is dependent on the plant source, and it typically contains saccharides at 5-20 wt. % that complex (weakly bind) to the polymer structure. Macroalgae contains 30-40 wt. % alginate, which is a linear polymer of guluronic and mannuronic acids, typically in the sodium salt form.

The disclosed process to produce FDCA from pectin can include several steps, for example 1) pectin extraction from sugar beet pulp; 2) pectin hydrolysis to galacturonic acid; 3) oxidation of galacturonic acid to galactaric acid; 4) dehydration and cyclization of galactaric acid to FDCA, and 5) recovery and purification of FDCA. Relevant reactions for formation of the target FDCA from biomass pectins are given in Scheme 1 (which also illustrates an alternative route based on HMF described above). The monomer galacturonic acid, liberated from pectin by hydrolysis, can be oxidized to galactaric acid. FDCA can be then formed by acid-catalyzed C2-O5 cyclization of galactaric acid with loss of water to form the five-membered ring structure, followed by two additional dehydration steps to remove hydroxyl groups (—OH) at the C3 and C4 positions to form the furanic ring in FDCA. The FDCA formed can be then recovered and purified as a final product.

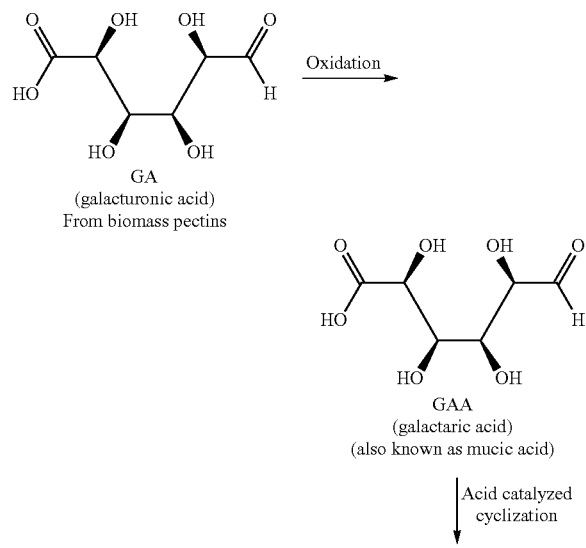

Scheme 1. Formation of FDCA from Biomass Pectins.

GA (galacturonic acid) From biomass pectins

GAA (galactaric acid) (also known as mucic acid)

Acid catalyzed cyclization

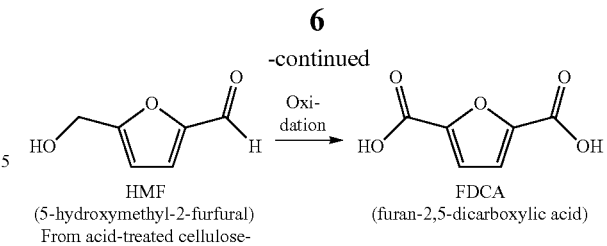

HMF (5-hydroxymethyl-2-furfural) From acid-treated cellulose- or starch-derived hexoses FDCA (furan-2,5-dicarboxylic acid)

As described in more detail below in Example 1, several experiments were performed to dehydrate galactaric acid (the pectin-based precursor) to FDCA in an ionic liquid (1-butyl-3-methyl-imidizolium hydrogen sulfate) and sulfuric acid solution. Typical results for experiments conducted at 115° C. and reduced pressure for 16-20 hours are given in Table 2. It was found recently that an FDCA yield of 52% of theoretical could by achieved at conditions of high galactaric acid concentration of approximately 25 wt. % of solution (R-7-8-15). Repetition of the experiment (R-10-15-15) gave a similar yield (see Table 2 below).

Table 2

Experiment Summary for Formation of FDCA

| Experiment | Mucic Acid (g) | Ionic Liquid (g) | Sulfuric Acid (g) | FDCA Yield (%) |
|---|---|---|---|---|
| R-6-24-15 | 0.245 | 4.09 | 2.38 | 17 |
| R-6-30-15 | 1.084 | 4.07 | 2.43 | 25 |
| R-7-8-15 | 2.03 | 4.05 | 2.52 | 52 |
| R-10-15-15 | 2.05 | 4.11 | 2.49 | 46 |

In another experiment, galactaric acid was mixed into a melt of p-toluenesulfonic acid (PTSA), an acid with similar acid strength to sulfuric acid but without the oxidative properties of sulfuric acid. No ionic liquid was used in this experiment. After a typical reaction period (20 hr), the resulting solution was analyzed and an FDCA yield of 46% was obtained. This experiment illustrates the potential to achieve higher yields of FDCA through manipulation of the acid species and acid concentration in the reaction mixture.

Further description related to the disclosed methods may be found in U.S. Publication No. 2014/0295508 and U.S. Publication No. 2015/0086721, which are incorporated herein by reference in their entireties. U.S. Publication No. 2014/0295508 is directed to other methods for forming FDCA, and contains description related to various biomass materials and related methods that can be used to obtain alginate and/or pectin as an intermediate material to form aldaric acids for use according to methods of the present disclosure. U.S. Publication No. 2015/0086721 is directed to nanoparticle dispersions with ionic-liquid stabilizers, and contains description related to ionic liquids that can be used as an ionic liquid reaction medium component/solvent for use according to the methods of the present disclosure, for example including aromatic heterocyclic rings suitable as an ionic liquid cationic moiety, counter anions suitable for the ionic liquid, and organic substituents $R_1$-$R_5$ or $R_6$ which are suitable for attachment to the cationic moiety as part of the ionic liquid structure.

EXAMPLES

The following examples illustrate the disclosed methods for forming FDCA, but they are not intended to limit the scope thereof.

Example 1

The formation of 2,5-furan dicarboxylic acid from glucaric or galactaric acids via cyclization and dehydration is carried out in an ionic liquid solvent. Glucaric and galactaric acids are formed by oxidation of glucuronic and alginic acids, which are obtained from pectins and macroalgae, both relatively underutilized biomass resources. 2,5-Furandicarboxylic acid is the major building block of polyethylenefuranoate ester (PEF) polymers, analogs to polyethylene terephthalate esters (PETE) that constitute the majority of plastic for drink bottle containers worldwide. PEF polymers have significantly better vapor barrier properties than PETE, thus making them candidates for packaging materials where PETE is not suitable. The improved barrier properties of PEF will open new applications for plastic containers (alcoholic beverages, etc.) and extend food shelf life.

The formation of 2,5-furandicarboxylic acid (FDCA) from C6 biomass carbohydrates is attracting a great deal of attention among researchers in the biomass conversion field, as it is a component of polyethylene furanoate ester (PEF) polymer that has attractive properties. Most effort in the field is centered around the dehydration of glucose or (more easily) fructose to form hydroxymethyl furfural (HMF), which is then oxidized to FDCA. There are two challenges with this route at present: one is that HMF is a difficult molecule to isolate, because it has low volatility and low decomposition temperature. The second is that the oxidation of HMF to FDCA is not particularly efficient and requires precious metal catalysts.

This example illustrates a different route to FDCA, not via HMF but via dehydration and cyclization of C6 dicarboxylic acids. The C6 dicarboxylic acids glucaric acid and galactaric acid, also known as saccharic acid and mucic acid, respectively, or more generally as aldaric acids, are not readily obtained from glucose. This is because glucose can be easily oxidized to gluconic acid (carboxylic acid group at C1, hydroxyl group at C6), but is not readily or selectively oxidized further at the C6 position to the dicarboxylic acid. Thus cellulosic biomass or starch, both polymers of glucose, are not good feedstocks for aldaric acid formation. Fortunately, other biomass sources, specifically pectin and macroalgae that have as carbohydrate building blocks glucuronic acid or alginic acid, can be oxidized to the dicarboxylic acids. These biomass sources are historically considered less valuable and less abundant than cellulosic or starch feed stocks, but their alternative carbohydrate structures make them attractive for chemicals and polymers production.

The overall reaction pathway for formation of the target 2,5-furandicarboxylic acid (FDCA) is given in Scheme 1 above. The biomass sources can be hydrolyzed to monomer glucuronic or alginic acids, and then oxidized under pH control to the aldaric acids. These aldaric acids, specifically glucaric and galactaric acid, are six-carbon dicarboxylic acids with hydroxyl groups on each of the four interior carbons. FDCA is formed by C2-O5 cyclization of the aldaric acid with loss of water to form the five-membered ring structure, followed by two additional dehydration steps to remove —OH at C3 and C4 and form the furanic ring.

The example includes the cyclization and dehydration of aldaric acids to 2,5-FDCA in an ionic liquid solvent in the presence of sulfuric acid as a dehydration catalyst. The ionic liquid solvent that we have used in these experiments is 1-butyl-3-methylimidazolium sulfate; with an ionic liquid, the reaction proceeds to meaningful yields in the presence of at least a stoichiometric equivalent of sulfuric acid.

Procedure:

The following procedure is used for the production of FDCA from mucic (galactaric) and saccharic (glucaric) acids in the presence of ionic liquid as a reaction solvent.

Drying of ionic liquid: Place desired quantity of ionic liquid (1-butyl-3-methylimidazolium sulfate) in a weighed 50 ml three-neck reaction vessel. Place a three-way glass valve on the middle neck of the vessel to control the reaction environment as under vacuum or at atmospheric pressure under inert gas. The second side neck is sealed with a glass stopper. The third neck is fitted with a rubber stopper fitted with flexible tubing connected to a nitrogen cylinder to allow flow of nitrogen purge gas into the vessel. Nitrogen purge limits contact of the ionic liquid with water which has a deleterious effect on the reaction. Once the vessel is sealed and purged, the vessel with ionic liquid is heated to 60° C. under vacuum in a stirred oil bath and maintained at that temperature until bubbling within the ionic liquid ceases (typically 20 minutes). Cool the reaction vessel to room temperature and purge with nitrogen. Weigh to determine dry weight of ionic liquid added.

Adding reagents to vessel: Weigh out the desired substrate (mucic acid or saccharic acid) in the quantity desired for the experiment (1 g substrate for each 5 g of ionic liquid in most experiments). Add the substrate to the ionic liquid by briefly removing the glass stopper on the three-neck vessel. Add sulfuric acid in an amount equal to one to three molar equivalents of the dicarboxylic acid substrate, also through the opening of the glass stopper on the three-neck vessel. Replace the stopper to minimize exposure of the reaction mixture to the atmosphere and water.

Reaction of substrate: Return the vessel to the oil bath set to the desired reaction temperature. Connect the flexible tubing to the nitrogen cylinder and the vacuum line to the three-way valve. Slowly bring the vessel under vacuum to an absolute pressure of less than 1.0 mm Hg; during the evacuation reduce pressure slowly to avoid bubbling and deposition of the reaction mixture on the vessel walls. Allow the reaction to proceed for the desired length of time (10-40 hr) at reaction temperature.

Analysis: At certain points during reaction and at the end of reaction, samples were taken from the reaction mixture for analysis. The reaction sample was diluted for HPLC analysis in one of two ways: 1) the sample was neutralized with 1.0 M NaOH solution and then further diluted with water to solubilize the ionic liquid and all substrates and products (including FDCA as the sodium salt); or 2) the sample was directly dissolved in dimethyl sulfoxide (DMSO) for analysis. The extent of dilution in each experiment ranged from 5× to 30× to bring the diluted sample concentrations within the appropriate range for analysis using ELSD and UV detectors. The conversion of the substrate dicarboxylic acid and formation of FDCA was monitored via analysis of the reaction mixture by high performance liquid chromatography (HPLC). The method uses a Hypercarb 3.0μ 100 mm×3 mm HPLC column at 60° C. with a mobile phase gradient starting with 0.2 wt % trifluoroacetic acid (TFA) in water for two minutes, then a linear gradient to 0.2 wt % TFA in methanol from t=2 minutes to t=15 minutes, followed by holding at the 0.2 wt % TFA in methanol for 10 minutes. Total mobile phase flow rate is 0.65 ml/min. With this chromatography method (projectgreen2b), the peak for mucic acid elutes at 2.5 minutes; the peak for saccharic acid elutes at 7.5 minutes, and the peak for FDCA elutes at 18 minutes. Use of external calibration standards allows the concentration of each species to be determined in the reaction sample.

Results:

Several experiments were conducted to convert saccharic acid and mucic acid to FDCA in the ionic liquid solvent. These experiments are summarized in Table 3 below.

TABLE 3

Results of FDCA Formation Experiments in Ionic Liquid Solvent

| Sample | H2SO4 equiv. | Substrate | Substrate acid equiv. mass (g) | Ionic liquid mass (g) | Solvent/ substrate ratio | RXN temp. (° C.) | RXN time (hr) | FDCA yield (%) | RXN vacuum? |
|---|---|---|---|---|---|---|---|---|---|
| R5-pdt | 1 | Saccharic acid | 1.7287 | 6.2492 dry | 3.6 | 130 | 13 | 28 | Y |
| IL-R6-S1 | 0.5 | Saccharic acid | 1.4569 | 6.3148 dry | 4.3 | 150 | 4 | 0 | Y |
| IL-R7-S1 | 0.5 | Mucic acid | 1.3208 | 5.7702 dry | 4.4 | 150 | 4 | 6 | Y |
| IL-R8-S2 | 0.5 | Mucic acid | 0.2164 | 1.4087 wet | 6.5 | 95 | 7 | 0.15 | N |
| IL-R9 | 0.5 | Saccharic acid | 0.2846 | 1.2114 wet | 4.3 | 95 | 7 | 0 | N |
| IL-R10-S3 | 1 | Mucic acid | 0.7662 | 4.026 wet | 5.3 | 120 | 41 | 10 | Y |
| IL-R11-S3 | 1 | Saccharic acid | 0.8525 | 4.9455 wet | 5.8 | 120 | 41 | 22 | Y |
| IL-R12-S1 | 2 | Mucic acid | 0.6701 | 3.3489 wet | 5.0 | 130 | 19 | 12 | Y |
| IL-R13-S1 | 2 | Saccharic acid | 0.5647 | 3.3905 wet | 6.0 | 130 | 19 | 14 | Y |
| IL-R14-S1 | 2 | Mucic acid | 0.6593 | 3.2878 wet | 5.0 | 120 | 17 | 27 | Y |
| IL-R15-S1 | 2 | Saccharic acid | 0.6833 | 3.9616 wet | 5.8 | 120 | 17 | 39 | Y |
| IL-R16 | 3 | Mucic acid | 0.6848 | 3.4769 dry | 5.1 | 120 | 20 | 13 | Y |
| IL-R17 | 3 | Saccharic acid | 0.5981 | 3.5095 dry | 5.9 | 120 | 20 | 16 | Y |
| IL-R18 | 2 | Saccharic acid | 0.8467 | 4.9004 dry | 5.8 | 120 | 21 | 13 | Y |
| IL-R19 | 2 PTSA | Saccharic acid | 0.7712 | 4.5709 dry | 5.9 | 120 | 21 | 4 | Y |
| IL-R20 | 2 | Mucic acid | 0.5912 | 2.8867 dry | 4.9 | 110 | 21 | 7 | Y |
| IL-R21 | 2 | Saccharic acid | 0.6397 | 3.1964 dry | 5.0 | 110 | 21 | 6 | Y |
| IL-R24 | 2 | Saccharic acid | 0.3125 | 1.5349 dry | 4.9 | 120 | 16 | 14 | Y |

It can be seen that reaction takes place around 120° C. typically overnight. Disappearance of the dicarboxylic acid substrates takes place very rapidly once in the reaction medium at reaction temperature. The verified yield of FDCA from HPLC is as high as 39% of the theoretical limit in these initial studies.

Sample chromatograms from the first reaction sample taken in the course of Experiments 14 and 15 (Table 3) were taken. The complete conversion of the starting materials mucic acid and saccharic acid was observed, as is the presence of FDCA as the primary product.

It was observed that desired product FDCA possibly sublimes in the temperature range of reaction, lowering recovery of the FDCA product. Several control reactions starting with FDCA in the ionic liquid were conducted to characterize the sublimation of FDCA during reaction. Details of these control experiments are given in Table 4 below.

TABLE 4

Summary of control experiments in ionic liquid reaction system

| Control Experiment | Substrate | Mass Substrate (g) | Mass Ionic Liquid (g) | H2SO4 added (uL) | Temp (° C.) | Result |
|---|---|---|---|---|---|---|
| 1 | FDCA | 0.0759 | 0.5086 | 52 | 130 | FDCA recovery 30-50% (4 samples) |
| 2 | FDCA | 0.1025 | 3.1731 | 70 | 130 | FDCA recovery 50-95% (4 samples) |
| 3 | Saccharic acid (K+) | 0.6903 | 2.897 | 0 | 60 | Saccharic acid observed, HPLC peaks too concentrated |
| 4 | Saccharic acid (K+) | 0.0961 | 1.592 | 0 | 60 | Saccharic acid observed but recovery low |

TABLE 4-continued

Summary of control experiments in ionic liquid reaction system

| Control Experiment | Substrate | Mass Substrate (g) | Mass Ionic Liquid (g) | H2SO4 added (uL) | Temp (° C.) | Result |
|---|---|---|---|---|---|---|
| 5 | Mucic acid (Na+) | 0.271 | 1.355 | 0 | N/A | Reaction abandoned |
| FDCA Subl. | FDCA | 0.0818 | 0 | 0 | 80-150 | Approximately 50% of FDCA placed in reactor sublimed |

Results of the FDCA control experiments (1 and 2, Table 4) show that FDCA sublimed and then condensed as a white solid on the cold surfaces of the reaction vessel. This was verified by HPLC analysis of the recovered white powder, in which the FDCA peak is the only peak present other than salts and the ionic liquid. The above experiment, "FDCA Subl.," shows that approximately half of the FDCA initially placed in the reactor vessel sublimed during the course of an equivalent time-temperature experiment. This result may explain the low yields shown in Table 3 in which FDCA possibly sublimed from the ionic liquid reaction mixture and condensed, unseen, in the exhaust vacuum line from the reactor.

In the representative example, the ionic liquid 1-butyl-3-methylimidazolium sulfate is a good reaction environment for the cyclization and dehydration of the aldaric acids mucic acid and galactaric acid. The reaction takes place at high concentrations of the aldaric acid, 20 wt % of the ionic liquid solution, with 1-3 stoichiometric equivalents of $H_2SO_4$ at temperatures from 90-130° C. Moderate yields of FDCA, up to 40% of theoretical, have been obtained. Possible FDCA sublimation could have led to product forming on the cold walls of the reactor vessel, thereby resulting in a measured yield lower than that actually generated by the reaction.

Follow on work to this example includes examination of the relative quantities of aldaric acid, ionic liquid, and sulfuric acid used in the experiments.

A number of experiments were conducted at different conditions with the goal of looking at sensitivity of the reaction to various parameters and quantities of materials used. Yields of FDCA from mucic and saccharic acid are in the range of 20-35% for a range of reaction conditions (RE-6 through RE-11 and R-6-8-15 through R-7-6-2015 in Table 5) without any clear trend in FDCA yield obtained. In a further experiment (R-7-8-15), twice the usual quantity of initial mucic acid was used and an FDCA yield of 52% of theoretical was achieved, a value significantly higher than any we had achieved previously. It is interesting to note that the second highest yield achieved (Experiment R-6-8-15, Table 5) was 27% of theoretical for an experiment with the same proportions of aldaric acid, sulfuric acid, and ionic liquid as R-7-8-15, but at twice the scale. One final note on FDCA recovery: the simple addition of water to the reaction medium at the end of reaction leads to dissolution of the ionic liquid and $H_2SO_4$, but precipitation of FDCA is observed. This method of recovering FDCA could prove inexpensive and useful, as subsequent removal of water could make recycling of the ionic liquid and sulfuric acid possible.

TABLE 5

Supplemental Experiments

| Reaction ID | Substrate | Temp. (° C.) | H2SO4 Equiv. | AA/(AA + IL) % Sub. | Time of Exp. (hr) | Aldaric Acid Mass (g) | Ionic Liquid Mass (g) | H2SO4 Mass (g) | FDCA Yield (% theor.) |
|---|---|---|---|---|---|---|---|---|---|
| R-2 | Mucic Acid | 130 | 2.26 | 18.5% | 18:00 | 0.825 | 3.637 | 0.868 | 23.4% |
| RE-1B | Mucic Acid | 123 | 2.27 | 18.5% | 3:01 | 0.458 | 2.015 | 0.485 | 4.1% |
| RE-1C | Mucic Acid | 125 | 1.27 | 17.1% | 6:30 | 0.430 | 2.088 | 0.254 | 4.4% |
| RE-2 | Mucic Acid | 129 | 1.10 | 18.6% | 22:25 | 0.467 | 2.042 | 0.240 | 9.9% |
| RE-3 | Mucic Acid | 130 | 3.67 | 16.2% | 22:20 | 0.419 | 2.172 | 0.717 | 7.4% |
| RE-5 | Mucic Acid | 150 | 2.10 | 19.9% | 22:00 | 0.478 | 1.921 | 0.469 | 20.5% |
| R-2S.A. | Saccharic Acid | 130 | 1.94 | 19.0% | 20:45 | 0.526 | 2.245 | 0.476 | 11.4% |
| R-M.A. Cont | Mucic Acid | 60 | 2.27 | 18.9% | 22:20 | 0.425 | 1.822 | 0.451 | 0.0% |
| ISO-1 | Mucic Acid | 130 | 1.57 | 20.3% | 45:00 | 0.544 | 2.132 | 0.399 | 15.9% |
| IL-R15-S1-II A | Saccharic Acid | 120 | 3.09 | 13.9% | 21:00 | 0.655 | 4.049 | 0.945 | 20.9% |
| IL-R15-S1-II B | Saccharic Acid | 120 | 2.63 | 13.8% | 20:40 | 0.648 | 4.038 | 0.794 | 17.8% |
| IL-R15-S1-II C | Saccharic Acid | 120 | 2.53 | 14.3% | 17:00 | 0.666 | 3.999 | 0.787 | 10.4% |
| IL-R15-S1-II CA | Saccharic Acid | 120 | 2.50 | 14.6% | 17:00 | 0.676 | 3.963 | 0.787 | 9.8% |
| IL-R15-S1-II D | Saccharic Acid | 120 | 2.00 | 14.0% | 17:00 | 0.610 | 3.745 | 0.569 | 7.6% |
| RE-6 | Mucic Acid | 120 | 3.06 | 19.0% | 18:35 | 0.982 | 4.183 | 1.401 | 20.3% |
| RE-6 S.A. | Saccharic Acid | 120 | 3.67 | 17.5% | 18:35 | 0.850 | 4.006 | 1.456 | 18.8% |
| RE-7 | Mucic Acid | 120 | 3.10 | 19.1% | 20:27 | 0.967 | 4.104 | 1.399 | 27.3% |
| RE-8 | Mucic Acid | 115 | 5.13 | 19.3% | 18:55 | 0.961 | 4.010 | 2.303 | 33.4% |
| RE-8W.V. | Mucic Acid | 115 | 4.86 | 18.7% | 20:35 | 0.952 | 4.148 | 2.158 | 26.0% |
| RE-9 | Mucic Acid | 116 | 6.54 | 19.7% | 20:00 | 0.986 | 4.009 | 3.010 | 24.4% |
| RE-10 | Mucic Acid | 116 | 6.00 | 0.0% | 4:12 | 0.000 | | 0.000 | 0.0% |
| RE-11 | Mucic Acid | 109 | 5.23 | 19.5% | 22:33 | 0.963 | 3.983 | 2.349 | 26.8% |
| R6-3-15 | Mucic Acid | 112 | 4.97 | 18 | 19 | 0.4856 | 2.2149 | 1.1492 | 13 |
| RNIL-6-4-15 | Mucic Acid | 115 | 4.82 | 20.1 | 19.35 | 0.5079 | 2.0163 | 1.1651 | 10 |
| R-6-8-15 | Mucic Acid | 115 | 2.49 | 33.9 | 20 | 4.1334 | 8.065 | 4.892 | 27 |
| R-6-11-15 | Mucic Acid | 115 | 4.9 | 20.3 | 20 | 1.052 | 4.037 | 2.399 | 20 |
| R-6-18-15 | Mucic Acid | 110 | 4.8 | 20.8 | 23 | 1.0544 | 4.003 | 2.4276 | 20 |
| R-6-24-15 | Mucic Acid | 115 | 4.9 | 20.2 | 22 | 1.0368 | 4.0987 | 2.4364 | 20 |

TABLE 5-continued

Supplemental Experiments

| Reaction ID | Substrate | Temp. (° C.) | H2SO4 Equiv. | AA/(AA + IL) % Sub. | Time of Exp. (hr) | Aldaric Acid Mass (g) | Ionic Liquid Mass (g) | H2SO4 Mass (g) | FDCA Yield (% theor.) |
|---|---|---|---|---|---|---|---|---|---|
| R-6-24-15 | Mucic Acid | 115 | 20.3 | 5.6 | 22 | 0.2454 | 4.087 | 2.377 | 17 |
| R6-29-15 | Mucic Acid | 115 | 33.8 | 3.7 | 23 | 0.1563 | 4.074 | 2.512 | 8 to 14 |
| R6-30-15 | Mucic Acid | 115 | 4.7 | 21 | 25.6 | 1.0844 | 4.069 | 2.429 | 25 |
| R-7-6-15 | Mucic Acid | 115 | 4.83 | 20.5 | 25.5 | 1.045 | 4.065 | 2.4062 | 23 |
| R-7-8-15 | Mucic Acid | 115 | 2.6 | 33.1 | 16.7 | 2.003 | 4.051 | 2.52 | 52 |

Example 2—Continuous Process for Making FDCA

A proposed continuous process concept for the production of FDCA from agriculturally-based pectin is outlined below.

Process Step 1—

Pectin extraction from biomass pulp: The extraction and isolation of pectins from sugar beet pulp and apple pomace is commercially practiced, and thus is well understood. Briefly, the use of dilute acid (0.1M HCl) alone achieves approximately 65% pectin dissolution into the aqueous medium, while co-addition of a commercial blend of enzymes gives >90% dissolution. Following filtration of undissolved pulp residue, pectin can be precipitated by addition of two volumes of ethanol to each volume of aqueous medium and then filtered, but this step may not be required in the proposed process. Literature values of liquid flows, acid strength, enzyme loading, extraction time, etc. can be used to select specific operating conditions for this step.

Process Step 2—

Pectin hydrolysis to galacturonic acid: Following extraction from pulp, pectin (either as filtered solid or in acid/enzyme solution) can be subjected to another dilute acid solution (0.2-0.5 M HCl) to hydrolyze the α-1,4-bonds and liberate galacturonic acid, which is water soluble. These hydrolysis conditions will also liberate acetic acid, methanol, and small amounts of saccharide monomers that are present in the pectin structure. Again, this step is reported in the literature, which can be used to select specific operating conditions for this step.

Process Step 3—

Oxidation of galacturonic acid to galactaric acid: This aqueous phase oxidation step has been demonstrated in earlier work. The galacturonic acid solution from the prior step will be subjected to process conditions that mimic those from the earlier work—molecular $O_2$, Bi—Pt/C catalyst, and pH control with NaOH addition. These conditions will produce the sodium salt of galactaric acid as the oxidation product. Following oxidation, the catalyst will be filtered off for recycling, and excess HCl will be added to the reaction to liberate and precipitate free galactaric acid, which is water insoluble. Following filtration to recover galactaric acid, the remaining reaction solution, which can contain NaCl, methanol, acetic acid, small amounts of saccharides, and may contain residual enzyme from step 1, can be further processed to recover valued byproducts or processed for disposal.

Process Step 4—

Dehydration of galactaric acid to FDCA: Solid galactaric acid can be processed according to the disclosed methods, for example by mixing with 1-butyl-3-methyl-imidizolium hydrogen sulfate as an ionic liquid and sulfuric acid as an acid catalyst to initiate the dehydration reaction to FDCA. Conditions established in Example 1 above can be used for this step.

Process Step 5—

Recovery of FDCA: Following FDCA formation, the reaction medium can be mixed with water to precipitate FDCA. The FDCA formed can be filtered and washed as the final product of the process, while the residual solution of ionic liquid and sulfuric liquid can be cleaned and then dried for recycling back to the dehydration unit.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

REFERENCES

1. Burgess, S.; Karvan, O.; Johnson, J.; Kriegel, R.; Koros, W. "Oxygen sorption and transport in amorphous poly (ethylene furanoate)," Polymer 2014, 55, 4788-4756.
2. Burgess, S.; Leisen, J.; Kraftschik, B.; Mubarak, C.; Kriegel, R.; Koros, W. "Chain mobility, thermal, and mechanical properties of poly(ethylene furanoate) compared to poly(ethylene terephthalate," Macromolecules 2014, 37, 1383-1391.
3. Yu, Z. L.; Zhou, J. D.; Cao, F.; Wen, B. B.; Zhu, X.; Wei, P., "Chemosynthesis and characterization of fully biomass-based copolymers of ethylene glycol, 2,5-furandicarboxylic acid, and succinic acid" J. Appl. Polym. Sci. 2013, 130, 1415-1420.
4. Pedersen, A.; Ringborg, R.; Grotkjaer, T.; Pedersen, S; Woodley, J. "Synthesis of 5-hydroxymethylfurfural (HMF) by acid-catalyzed dehydration of glucose-fructose mixtures," Chemical Engineering Journal 2015, 273, 455-464.
5. Kurian, J. D.; Nair, G. R.; Hussain, A.; Raghavan, GSV." Feedstocks, logistics and pre-treatment processes for sustainable lignocellulosic biorefineries: A comprehensive review." Renewable and Sustainable Energy Reviews 2013, 25, 205-219.
6. Jadhav, A.; Chinnappan, A.; Patil, R.; Kostjuk, S.; Kim, H. "Green chemical conversion of fructose into 5-hydroxymethylfurfural (HMF) using unsymmetrical dicationic ionic liquids under mild reaction conditions," Chemical Engineering Journal 2014, 243, 92-98.
7. Tong, X.; Ma, Y.; Li, Y. "Biomass into chemicals: conversion of sugars to furan derivatives by catalytic processes," Applied Catalysis A: General 2010, 385, 1-13.
8. Dutta, S.; De, S.; Saha, B. "A brief summary of the synthesis of polyester building-block chemicals and biofuels from 5-hydroxymethylfurfural," Chem. Phys. Chem 2012, 77, 1-15.
9. Koopman, F.; Wierckx, N.; deWinde, J.; Ruijssenaars, H. "Efficient whole-cell biotransformation of 5-hydroxymethylfurfural into FDCA, 2,5-furandicarboxylic acid," Bioresource Technol. 2010, 101, 6291-6296.
10. Albonetti, S.; Lolli, A.; Morandi, V.; Migliori, A.; Lucarelli, C.; Cavani, F. "Conversion of 5-hydroxymethylfurfural to 2,5-furandicarboxylic acid over Au-based catalysts: Optimization of active phase and metal-support interaction," Applied Catalysis B: Environmental 2015, 163, 520-530.
11. Gao, L.; Deng, K.; Zheng, J.; Liu, B.; Zhang, Z. "Efficient oxidation of biomass derived 5-hydroxymethlfurfural into 2,5-furandicarboxylic acid catalyzed by Merrifield resin supported cobalt porphyrin," Chemical Engineering Journal 2015, 270, 444-449.
12. Lolli, A.; Albonetti, S.; Utili, L.; Amadori, R.; Ospitali, F.; Lucarelli, C.; Cavani, F. "Insights into the reaction mechanism for 5-hydroxymethylfurfural oxidation to FDCA on bimetallic Pd—Au nanoparticles," Applied Catal. A: General 2015, 504, 408-419.
13. Jain, A.; Jonnalagadda, S.; Ramanujachary, K.; Mugweru, A. "Selective oxidation of 5-hydoxymethyl-2-furfural to furan-2,5-dicarboxylic acid over spinel mixed metal oxide catalyst," Catalysis Commun. 2015, 58, 179-182.
14. Miura, T.; Kakinuma, H.; Kawano, T.; Matsuhisa, H. "Method for producing furan-2,5-dicarboxylic acid," U.S. Pat. No. 7,411,078 (2008). (Canon patent with metal permangeanate salt homogeneous, high yield)
15. Yutaka, K; Toshinari, M.; Eritate, S.; Komuro, T. "Method of producing 2,5-furandicarboxylic acid," U.S. Pat. No. 8,242,292 (2012).
16. Lew, B.; "Method of producing dehydromucic acid," U.S. Pat. No. 3,326,944 (1967).
17. Zhang, J.; Li, J.; Tang, Y.; Lin, Lu; Long, M. "Advances in catalytic production of bio-based polyester monomer 2,5-furandicarboxylic acid derived from lignocellulosic biomass," Carbohydrate Polymers 2015, 130, 420-428.
18. Taguchi, Y.; Oishi, A.; Iida, H., "One-step Synthesis of Dibutyl Furandicarboxylates from Galactaric Acid," Chem. Lett. 2008, 237, 50-51.
19. Vilela, C.; Sousa, A.; Fonseca, A.; Serra, A.; Coelho, J.; Freire, C.; Silvestre, A. "The quest for sustainable polyesters—insights into the future,"

What is claimed is:

1. A method for forming 2,5-furan dicarboxylic acid (FDCA), the method comprising:
providing a reaction medium comprising a 6-carbon aldaric acid, an acid catalyst, and an ionic liquid; and
dehydrating and cyclizing the aldaric acid in the reaction medium to form 2,5-furan dicarboxylic acid (FDCA) as a reaction product.

2. The method of claim 1, wherein the aldaric acid is selected from the group consisting of galactaric acid.

3. The method of claim 2, further comprising:
oxidizing galacturonic acid to form galactaric acid; and
adding the galactaric acid to the reaction medium.

4. The method of claim 2, further comprising:
extracting pectin from a biomass material;
hydrolyzing the pectin to form galacturonic acid;
oxidizing the galacturonic acid to form galactaric acid; and
adding the galactaric acid to the reaction medium.

5. The method of claim 4, wherein the biomass material is selected from the group consisting of sugarbeet pulp, apple pomace, citrus pulp, and combinations thereof.

6. The method of claim 1, wherein the aldaric acid is selected from the group consisting of gularic acid, mannaric acid, and combinations thereof.

7. The method of claim 6, further comprising:
oxidizing at least one of guluronic acid and mannuronic acid to form at least one of gularic acid and mannaric acid, respectively; and
adding the at least one of gularic acid and mannaric acid to the reaction medium.

8. The method of claim 6, further comprising:
extracting alginate from a biomass material;
hydrolyzing the alginate to form at least one of guluronic acid and mannuronic acid;
oxidizing the at least one of guluronic acid and mannuronic acid to form at least one of gularic acid and mannaric acid, respectively; and
adding the at least one of gularic acid and mannaric acid to the reaction medium.

9. The method of claim 8, wherein the biomass material comprises macro algae.

10. The method of claim 1, wherein the aldaric acid is selected from the group consisting of glucaric acid.

11. The method of claim 1, wherein the ionic liquid comprises a cationic moiety selected from the group consisting of a pyridinium, pyridazinium, pyrimidinium, pyrazinium, oxazinium, thiazinium, imidazolium, pyrazolium, thiazolium, isothiazolium, oxazolium, isoxazolium, and triazolium cationic moieties.

12. The method of claim 11, wherein the ionic liquid further comprises one or more organic substituents selected from the group consisting of alkyl groups and aryl groups.

13. The method of claim 11, wherein the ionic liquid further comprises a counter anion selected from the group consisting of sulfate, hydrogen sulfate, nitrate, fluoride, chloride, bromide, iodide, methyl sulfonate, and fluoroborate anions.

14. The method of claim 13, wherein the acid catalyst comprises an acid corresponding to the counter anion of the ionic liquid.

15. The method of claim 1, wherein the acid catalyst is selected from the group consisting of sulfuric acid, nitric acid, hydrofluoric acid, hydrochloric acid, hydrobromic acid, hydroiodic acid, methyl sulfonic acid, and fluoroboric acid.

16. The method of claim 1, wherein the acid catalyst is selected from the group consisting of a liquid phase organic sulfonic acid.

17. A method for forming 2,5-furan dicarboxylic acid (FDCA), the method comprising:
- providing a reaction medium comprising a 6-carbon aldaric acid and an acid catalyst; and
- dehydrating and cyclizing the aldaric acid in the reaction medium to form 2,5-furan dicarboxylic acid (FDCA) as a reaction product;
- wherein the reaction medium substantially free from water, the reaction medium containing less than 1 wt. % water before dehydrating and cyclizing the aldaric acid in the reaction medium to form the FDCA reaction product.

18. The method of claim 1, wherein the reaction medium is substantially free from alcohols, the reaction medium containing less than 1 wt. % alcohols before dehydrating and cyclizing the aldaric acid in the reaction medium to form the FDCA reaction product.

19. The method of claim 1, further comprising:
- separating the FDCA reaction product from the reaction medium.

20. The method of claim 1, comprising reacting and dehydrating the aldaric acid in the reaction medium at a temperature ranging from 50° C. to 200° C.

21. The method of claim 1, comprising reacting and dehydrating the aldaric acid in the reaction medium at a pressure equal to or less than atmospheric pressure.

* * * * *